United States Patent
Simonnet et al.

(10) Patent No.: US 6,461,625 B1
(45) Date of Patent: Oct. 8, 2002

(54) NANOEMULSION BASED ON ALKOXYLATED ALKENYL SUCCINATES OR ALKOXYLATED ALKENYL SUCCINATES OF GLUCOSE AND ITS USES IN THE COSMETICS, DERMATOLOGICAL, OPTHALMOLOGICAL AND/OR PHARMACEUTICAL FIELDS

(75) Inventors: Jean-Thierry Simonnet; Odile Sonneville, both of Paris; Sylvie Legret, Chatillon, all of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/489,839

(22) Filed: Jan. 24, 2000

(30) Foreign Application Priority Data

Feb. 2, 1999 (FR) .......................................... 99 01145

(51) Int. Cl.[7] .............................. A61K 6/00; A61K 7/00
(52) U.S. Cl. ...................... 424/401; 424/400; 424/450; 424/78.02; 424/78.03; 424/78.04; 514/552; 514/873; 514/844; 514/937; 514/938; 514/939
(58) Field of Search ........................... 424/78.02, 78.03, 424/78.04; 514/846, 880, 912, 937, 938, 941, 975; 516/20, 53

(56) References Cited

U.S. PATENT DOCUMENTS

| | | | |
|---|---|---|---|
| 5,098,606 A | * | 3/1992 | Nakajima et al. ............ 252/358 |
| 5,183,601 A | * | 2/1993 | Jisai et al. ................... 252/524 |
| 5,256,404 A | * | 10/1993 | Martino et al. ................ 424/59 |
| 5,753,241 A | * | 5/1998 | Ribier et al. ................. 424/401 |
| 5,798,331 A | * | 8/1998 | Anderson et al. ........... 510/501 |
| 5,993,793 A | * | 11/1999 | Simon et al. ............ 424/70.31 |

FOREIGN PATENT DOCUMENTS

| | | |
|---|---|---|
| EP | 0 813 860 | 12/1997 |

\* cited by examiner

Primary Examiner—Thurman K. Page
Assistant Examiner—Charesse L. Evans
(74) Attorney, Agent, or Firm—Oblon, Spivak, McClelland, Maier & Neustadt, P.C.

(57) ABSTRACT

A nanoemulsion, the oil globules of which have an average size of less than 100 nm, comprising a surfactant chosen from the alkoxylated alkenyl succinates, the alkoxylated alkenyl succinates of glucose and the alkoxylated alkenyl succinates of methylglucose, and at least one oil having a molecular weight of greater than 400, the ratio by weight of the amount of oily phase to the amount of surfactant ranging from 2 to 10. The emulsion obtained is transparent and stable on storage. It can comprise large amounts of oil while retaining good transparency and while having good cosmetic properties. It can constitute a composition for topical use, a pharmaceutical composition or an ophthalmological composition.

31 Claims, No Drawings

NANOEMULSION BASED ON ALKOXYLATED ALKENYL SUCCINATES OR ALKOXYLATED ALKENYL SUCCINATES OF GLUCOSE AND ITS USES IN THE COSMETICS, DERMATOLOGICAL, OPTHALMOLOGICAL AND/OR PHARMACEUTICAL FIELDS

BACKGROUND OF THE INVENTION

1. Field of the Invention

The present invention relates to a nanoemulsion based on a surfactant chosen from alkoxylated alkenyl succinates, alkoxylated alkenyl succinates of glucose and alkoxylated alkenyl succinates of methylglucose, and at least one oil having a molecular weight greater than 400, where the ratio by weight of the amount of oily phase to the amount of surfactant ranging from 2 to 10.

The invention also relates to a process for the preparation of the nanoemulsion and to its uses in the cosmetics, dermatological, ophthalmological and/or pharmaceutical fields. This nanoemulsion is stable on storage and can comprise large amounts of oil while retaining good transparency and while having good cosmetic properties.

2. Description of the Background

Nanoemulsions are oil-in-water emulsions, the oil globules of which have a very fine particle size, that is to say a number-average size of less than 100 nm. They are generally manufactured by mechanical fragmentation of an oily phase in an aqueous phase in the presence of a surfactant. In the case of nanoemulsions, the very small size of the oily globules is obtained in particular by virtue of at least one pass through a high-pressure homogenizer. The small size of the globules confers on them cosmetically advantageous properties which distinguish them from conventional emulsions: they are transparent and exhibit a novel texture. They can also carry active principles more efficiently.

Transparent microemulsions are known in the state of the art. In contrast to nanoemulsions, microemulsions are not, strictly speaking, emulsions; they are transparent solutions of micelles swollen by oil, which oil is generally a very-short-chain oil (e.g. hexane or decane) and is solubilized by virtue of the joint presence of a significant amount of surfactants and of cosurfactants which form the micelles. The size of the swollen micelles is very small owing to the small amount of oil which they can solubilize. This very small size of the micelles is the cause of their transparency, as with nanoemulsions. However, in contrast to nanoemulsions, microemulsions are spontaneously formed by mixing the constituents, without contributing mechanical energy other than simple magnetic stirring. The major disadvantages of microemulsions are related to their high proportion of surfactants, leading to intolerance and resulting in a sticky feel during application to the skin. Furthermore, their formulation range is generally very narrow and their temperature stability very limited.

In addition, nanoemulsions are known in the state of the art comprising an amphiphilic lipid phase composed of phospholipids, water and oil. These emulsions exhibit the disadvantage of being unstable on storage at conventional storage temperatures, namely between 0 and 45° C. They lead to yellow compositions and produce rancid smells which develop after several days of storage.

Nanoemulsions stabilized by a lamellar liquid crystal coating, obtained by the combination of a hydrophilic surfactant and of a lipophilic surfactant, are also known. However, these combinations are problematic to prepare. Furthermore, the nanoemulsions obtained exhibit a waxy and film-forming feel which is not very pleasant for the user.

Furthermore, the document EP-A-728,460 discloses nanoemulsions based on fluid nonionic amphiphilic lipids. However, these nanoemulsions exhibit the disadvantage of having a sticky effect during application to the skin.

The need therefore remains for nanoemulsions which have neither the disadvantages of those of the prior art nor the disadvantages of microemulsions.

SUMMARY OF THE INVENTION

The inventors have now discovered, unexpectedly, that the use of a surfactant chosen from alkoxylated alkenyl succinates, alkoxylated alkenyl succinates of glucose and alkoxylated alkenyl succinates of methylglucose, and of at least one oil having a molecular weight of greater than 400 (<400 grams per mole) makes it possible to obtain novel nanoemulsions exhibiting all the advantages of known nanoemulsions without their disadvantages.

Thus, the present invention provides a nanoemulsion comprising an oily phase dispersed in an aqueous phase and having oil globules with a number-average size of less than 100 nm, characterized in that it contains at least one surfactant chosen from the alkoxylated alkenyl succinates, the alkoxylated alkenyl succinates of glucose and the alkoxylated alkenyl succinates of methylglucose, and at least one oil having a molecular weight of greater than 400, and in that the ratio by weight of the amount of oily phase to the amount of surfactant ranges from 2 to 10.

The present invention also provides a method of caring for, treating and/or making up the skin, face and/or scalp, comprising applying the nanoemulsion to the skin, face and/or scalp.

The present invention also provides a method of caring for and/or treating the hair, comprising applying the nanoemulsion to the hair.

The present invention also provides a method of caring for and/or moisturizing the skin, mucous membranes and/or scalp, comprising applying the nanoemulsion to the skin, mucous membranes and/or scalp.

The present invention also provides a method of treating dry skin, comprising applying the nanoemulsion to the dry skin.

The present invention also provides a method of preparing the nanoemulsion.

A more complete appreciation of the invention and many of the attendant advantages thereof will be readily obtained as the same becomes better understood by reference to the following detailed description.

DETAILED DESCRIPTION OF THE INVENTION

The nanoemulsions according to the invention generally have a transparent to bluish appearance. Their transparency is measured by a transmittance coefficient at 600 nm ranging from 10 to 90% or else by a turbidity ranging from 60 to 600 NTU and preferably from 70 to 300 NTU, where the turbidity is measured with a Hach Model 2100 P portable turbidimeter.

The oil globules of the nanoemulsions of the invention have a number-average size of less than 100 nm and preferably ranging from 20 to 75 nm and more preferably from 40 to 60 nm. The decrease in the size of the globules makes it possible to promote the penetration of the active principles into the surface layers of the skin (carrier effect).

The surfactant which can be used in the nanoemulsion of the invention may be an alkoxylated alkenyl succinate, an alkoxylated alkenyl succinate of glucose, an alkoxylated alkenyl succinate of methylglucose or a mixture of these surfactants. According to a specific embodiment of the invention, the nanoemulsion of the invention is free of surfactant other than the alkoxylated alkenyl succinates, the alkoxylated alkenyl succinates of glucose and the alkoxylated alkenyl succinates of methylglucose.

The alkenyl succinates which can be used as surfactant in the nanoemulsion of the invention are in particular ethoxylated and/or propoxylated derivatives and they are preferably chosen from the compounds of formulae (I) or (II):

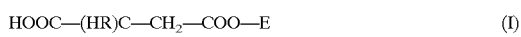

HOOC—(HR)C—CH$_2$—COO—E  (I)

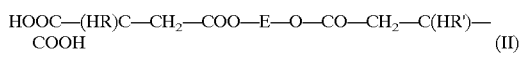

HOOC—(HR)C—CH$_2$—COO—E—O—CO—CH$_2$—C(HR')—COOH  (II)

in which:
the R and R' radicals are chosen from the linear or branched alkenyl radicals comprising from 6 to 22 carbon atoms,
E is chosen from the oxyethylenated chains of formula $(C_2H_4O)_n$, in which n ranges from 2 to 100, the oxypropylenated chains of formula $(C_3H_6O)_{n'}$, in which n' ranges from 2 to 100, the random or block copolymers comprising oxyethylenated chains of formula $(C_2H_4O)_n$ and oxypropylenated chains of formula $(C_3H_6O)_{n'}$, such that the sum of n and n' ranges from 2 to 100, the oxyethylenated and/or oxypropylenated glucose groups comprising on average from 4 to 100 oxyethylenated and/or oxypropylenated units distributed over all the hydroxyl functions, the oxyethylenated and/or oxypropylenated methylglucose groups comprising on average from 4 to 100 oxyethylenated and/or oxypropylenated units distributed over all the hydroxyl functions.

In formulae (I) and (II), n and n' are average values and are therefore not necessarily integers. A value ranging from 5 to 60 and still more preferably from 10 to 30 is advantageously chosen for n.

Advantageously, the R and/or R' radical is chosen from the linear alkenyl radicals comprising from 8 to 22 and preferably from 14 to 22 carbon atoms. This may be for example the hexadecenyl radical comprising 16 carbon atoms or the octadecenyl radical comprising 18 carbon atoms.

The compounds of formulae (I) and (II) described above in which E is chosen from the oxyethylenated chains, the oxypropylenated chains and the copolymers comprising oxyethylenated chains and oxypropylenated chains, may be prepared in accordance with the description which is given in the documents WO-A-94/00508, EP-A-107199 and GB-A-2131820, each incorporated herein for reference.

The acid function —COOH of the surfactants of formulae (I) and (II) is generally present in the nanoemulsion of the invention in a form which is neutralized by a neutralizing agent, the neutralizing agent being chosen, for example, from inorganic bases such as sodium hydroxide, potassium hydroxide, ammonia, and organic bases such as mono-, di- and triethanolamine, aminomethyl-1,3-propanediol, N-methylglucamine, basic amino acids such as arginine and lysine, and mixtures thereof.

By way of example of a surfactant which can be used in the nanoemulsion of the invention, there may be mentioned hexadecenyl succinate 18 EO (compound of formula I with R=hexadecenyl, E=$(C_2H_4O)_n$, n=18), hexadecenyl succinate 45 EO (compound of formula I with R=hexadecenyl, E=$(C_2H_4O)_n$, n=45), dihexadecenyl succinate 18 EO (compound of formula II with R=R'=hexa-decenyl, E=$(C_2H_4O)n$, n=1 8), dihexadecenyl succinate of glucose 10 EO (compound of formula II with R=R'=hexa-decenyl, E=oxyethylenated glucose comprising 10 oxyethylenated groups), dihexadecenyl succinate of glucose 20 EO (compound of formula II with R=R'=hexadecenyl, E=oxyethylenated glucose comprising 20 oxyethylenated groups), dioctadecenyl succinate of methylglucose 20 EO (compound of formula II with R=R'=octadecenyl, E=oxyethylenated methylglucose comprising 20 oxyethylenated groups), and mixtures thereof.

The amount of surfactant in the nanoemulsion of the invention can range, for example, from 0.2 to 15% by weight and preferably from 1 to 8% by weight with respect to the total weight of the nanoemulsion. This range includes all specific values and subranges therebetween, such as 0.5, 0.75, 2, 3, 5, 10 and 12% by weight.

The ratio by weight of the amount of the oily phase to the amount of surfactant ranges from 2 to 10 and preferably from 3 to 6. The term "amount of oily phase" is understood here to mean the total amount of the constituents of this phase without including the amount of surfactant.

The nanoemulsion according to the invention comprises at least one oil with a molecular weight of greater than 400. The oils with a molecular weight of greater than 400 can be chosen from oils of animal or vegetable origin, mineral oils, synthetic oils and silicone oils, and their mixtures. Mention may be made, as oils of this type, of, for example, isocetyl palmitate, isocetyl stearate, avocado oil or jojoba oil.

In addition, the oily phase can optionally comprise other oils and in particular oils having a molecular weight of less than 400. These oils are also chosen from oils of animal or vegetable origin, mineral oils, synthetic oils and silicone oils. Mention may be made, for example, as oils with a molecular weight of less than 400, of isododecane, isohexadecane, volatile silicone oils, isopropyl myristate, isopropyl palmitate or $C_{11}$–$C_{13}$ isoparaffin.

The oily phase can also comprise fatty substances other than the oils indicated above, such as fatty alcohols, for example stearyl, cetyl and behenyl alcohols, fatty acids, for example stearic, palmitic and behenic acids, oils of fluorinated type, waxes, gums and their mixtures.

The nanoemulsions of the invention comprise an amount of oily phase preferably ranging from 2 to 40% and better still from 5 to 30% by weight with respect to the total weight of the nanoemulsion, the proportion of oil(s) having a molecular weight of greater than 400 preferably representing at least 40% by weight of the oily phase.

According to a specific embodiment of the invention, the nanoemulsion of the invention additionally comprises one or more ionic amphiphilic lipids.

The ionic amphiphilic lipids which can be used in the nanoemulsions of the invention are preferably chosen from the group formed by anionic amphiphilic lipids and alkylsulfonic derivatives.

The anionic amphiphilic lipids can be more particularly chosen from the group formed by:
the alkaline salts of dicetyl and dimyristyl phosphate;
the alkaline salts of cholesterol sulfate;
the alkaline salts of cholesterol phosphate;
lipoamino acids and salts thereof, such as mono- and disodium acylglutamates, such as the disodium salt of N-stearoyl-L-glutamic acid sold under the name Acylglutamate HS21 by Ajinomoto;

the sodium salts of phosphatidic acid;
phospholipids.

The alkylsulfonic derivatives can more particularly be chosen from the alkylsulfonic derivatives of formula (V):

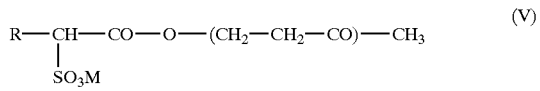

in which R represents an alkyl radical comprising from 16 to 22 carbon atoms, in particular the $C_{16}H_{33}$ and $CH_{18}H_{37}$ radicals, taken as a mixture or separately, and M is an alkali metal, such as sodium.

According to a preferred embodiment of the invention, a lipoamino acid is used as ionic amphiphilic lipid.

The ionic amphiphilic lipids can be introduced into one or other phase of the nanoemulsion. When they are present in the nanoemulsion of the invention, they can be used in concentrations preferably ranging from 0.01 to 5% by weight and more particularly from 0.25 to 1% by weight with respect to the total weight of the nanoemulsion.

The emulsions in accordance with the present invention can comprise additives for improving the transparency of the formulation.

These additives are preferably chosen from the group formed by:
 lower alcohols comprising from 1 to 8 carbon atoms and more particularly from 2 to 6 carbon atoms, such as ethanol;
 glycols, such as glycerol, propylene glycol, 1,3-butylene glycol, dipropylene glycol, pentylene glycol, isoprene glycol and polyethylene glycols comprising from 4 to 16 and preferably from 8 to 12 ethylene oxide units;
 sugars, such as glucose, fructose, maltose, lactose and sucrose.

These additives can be used as a mixture. When they are present in the nanoemulsion of the invention, they can be used at concentrations preferably ranging from 0.01 to 30% by weight with respect to the total weight of the nanoemulsion and better still from 5 to 20% by weight with respect to the total weight of the nanoemulsion. The amount of alcohol(s) and/or of sugar(s) preferably ranges from 5 to 20% by weight with respect to the total weight of the nanoemulsion and the amount of glycol(s) preferably ranges from 5 to 15% by weight with respect to the total weight of the nanoemulsion.

In addition, the use of the alcohols as defined above at concentrations greater than or equal to 15% by weight makes it possible to obtain preservative-free emulsions.

The nanoemulsions defined above can be used in any field where this type of composition is useful. They can constitute in particular compositions for topical use and in particular cosmetic or dermatological compositions. They can also be used as ophthalmic vehicles. They can in addition constitute in the pharmaceutical field a pharmaceutical composition which can be administered by the oral, parenteral or transcutaneous route.

Another subject-matter of the invention is therefore a composition for topical use, characterized in that it comprises a nanoemulsion as defined above.

A composition for topical or pharmaceutical use comprises a physiologically acceptable medium, that is to say compatible with the skin, mucous membranes, scalp, eyes and/or hair.

Another subject-matter of the invention is an ophthalmic vehicle, which comprises a nanoemulsion as defined above.

Another subject-matter of the invention is a pharmaceutical composition, which comprises a nanoemulsion as defined above.

The nanoemulsions of the invention may comprise water-soluble or fat-soluble active principles having a cosmetic, dermatological or ophthalmic activity. The fat-soluble active principles are in the oily globules of the emulsion, whereas the water-soluble active principles are in the aqueous phase of the emulsion. Mention may be made, by way of examples of active principles, of vitamins, such as vitamin E, and their derivatives and in particular their esters, provitamins, such as panthenol, humectants and sun-screen agents.

Mention may be made, as ophthalmic active principles, of, for example, antiglaucoma agents, such as betaxolol; antibiotics, such as acyclovir; antiallergics; anti-inflammatory agents, such as ibuprofen and its salts, diclofenac and its salts, or indomethacin; or antiviral agents.

The nanoemulsions in accordance with the invention can be provided in the form of a lotion, serum, cream, milk or toilet water and can comprise adjuvants commonly used in the cosmetics, dermatological and ophthalmic fields, such as, for example, gelling agents, preservatives, antioxidants and fragrances. They can also be provided in the form of an eye lotion, in particular for ophthalmological applications.

Mention may be made, among the gelling agents which can be used, of cellulose derivatives, algal derivatives, natural gums and synthetic polymers, such as polymers and copolymers of carboxyvinyl acids, for example those sold under the name Carbopol by Goodrich.

Another subject-matter of the invention is a process for the preparation of a nanoemulsion as defined above, this process comprising the mixing of the aqueous phase and the oily phase with vigorous stirring at a temperature ranging from 10 to 80° C. and then a homogenization of the mixture at a pressure preferably ranging from $6 \times 10^7$ Pa to $18 \times 10^7$ Pa (high-pressure homogenization). The shearing preferably ranges from $2 \times 10^6$ s$^{-1}$ to $5 \times 10^8$ s$^{-1}$ and better still from $1 \times 10^8$ s$^{-1}$ to $3 \times 10^8$ s$^{-1}$ (s$^{-1}$ signifies second$^{-1}$).

The nanoemulsion of the invention can be used, for example, for caring for, treating or making up the skin, face and/or scalp.

Another subject-matter of the invention is therefore the cosmetic use of the nanoemulsion as defined above for caring for, treating and/or making up the skin, face and/or scalp.

In addition, the nanoemulsion of the invention can also be used for caring for and/or treating the hair. It makes it possible to obtain a deposit of oil on the hair, which renders the latter glossier and more resistant to styling, without, however, making it lank. It also makes it possible, as a pretreatment, to improve the effects of dyeing or permanent waving.

Another subject-matter of the invention is therefore the cosmetic use of the nanoemulsion as defined above for caring for and/or treating the hair.

The nanoemulsion according to the invention makes possible in particular good moisturizing of the skin, mucous membranes and/or scalp and is particularly suited to the treatment of dry skin.

Another subject-matter of the invention is therefore a cosmetic process for caring for and/or moisturizing the skin, mucous membranes and/or scalp, characterized in that a nanoemulsion as defined above is applied to the skin, mucous membranes and/or scalp.

The invention also relates to the use of the nanoemulsion according to the invention in the manufacture of a dermatological composition intended for the treatment of dry skin.

Finally, the invention also relates to the use of the nanoemulsion according to the invention in the manufacture of an ophthalmological composition.

EXAMPLES

Having generally described this invention, a further understanding can be obtained by reference to certain specific examples which are provided herein for purposes of illustration only and are not intended to be limiting unless otherwise specified. The amounts shown are as % by weight.

Example 1

| Make-up removing fluid | |
|---|---|
| Oily phase: | |
| Disodium salt of N-stearoyl-L-glutamic acid (Acylglutamate HS21 Ajinomoto) | 0.5% |
| Isocetyl stearate (M.W. = 508) | 10% |
| Isopropyl myristate (M.W. = 270) | 5% |
| Aqueous phase: | |
| Dihexadecenyl succinate 18 EO (from ICI) | 4.5% |
| NaOH (1M) | 3% |
| Glycerol | 5% |
| Dipropylene glycol | 10 |
| Water | 62 |

A transparent nanoemulsion is obtained, the size of the globules of which is 55 nm and the turbidity of which is 211 NTU.

Example 2

| Make-up removing gel | |
|---|---|
| Oily phase: | |
| Disodium salt of N-stearoyl-L-glutamic acid (Acylglutamate HS21 from Ajinomoto) | 0.5% |
| Isocetyl stearate (M.W. = 508) | 20% |
| $C_{11}$–$C_{13}$ Isoparaffin (M.W. = 170) | 2.5% |
| Isohexadecane (M.W. = 226) | 2.5% |
| Aqueous phase: | |
| Hexadecenyl succinate 18 EO (from ICI) | 4.5% |
| NaOH (1M) | 1.5% |
| Glycerol | 5% |
| Dipropylene glycol | 10% |
| Water | 53.5% |

A gelled transparent nanoemulsion is obtained, the size of the globules of which is 54 nm and the turbidity of which is 130 NTU.

Obviously, numerous modifications and variations of the present invention are possible in light of the above teachings. It is therefore to be understood that within the scope of the appended claims, the invention may be practiced otherwise than as specifically described herein.

This application is based on French Patent Application Serial No. 99-01178, filed on Feb. 2, 1999, and incorporated herein by reference in its entirety.

What is claimed is:

1. A nanoemulsion, comprising:
    an oily phase dispersed in an aqueous phase and having oil globules with a number-average size of less than 100 nm,
    at least one surfactant selected from the group consisting of alkoxylated alkenyl succinates, alkoxylated alkenyl succinates of glucose and alkoxylated alkenyl succinates of methylglucose,
    at least one oil having a molecular weight of greater than 400 selected from the group consisting of oils of animal or vegetable origin, mineral oils, synthetic oils, silicone oils and mixtures thereof, and
    at least one oil having a molecular weight of less than 400,
    wherein the ratio by weight of the amount of oily phase to the amount of surfactant is 2 to 10.

2. The nanoemulsion of claim 1, which has a turbidity ranging from 60 to 600 NTU.

3. The nanoemulsion of claim 1, wherein the surfactant comprises 0.2 to 15% by weight of the nanoemulsion.

4. The nanoemulsion of claim 1, wherein the ratio by weight of the amount of oily phase to the amount of surfactant is 3 to 6.

5. The nanoemulsion of claim 1, wherein the oil globules have an average size of 20 to 75 nm.

6. The nanoemulsion of claim 1, wherein the surfactant is selected from the group consisting of compounds of formula (I) and (II):

$$HOOC-(HR)C-CH_2-COO-E \qquad (I)$$

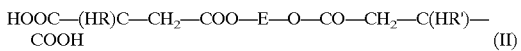

$$HOOC-(HR)C-CH_2-COO-E-O-CO-CH_2-C(HR')-COOH \qquad (II)$$

wherein
the R and R' radicals are linear or branched alkenyl radicals having 6 to 22 carbon atoms,
E is selected from the group consisting of oxyethylenated chains of formula $(C_2H_4O)_n$ in which n ranges from 2 to 100, oxypropylenated chains of formula $(C_3H_6O)_{n'}$, in which n' ranges from 2 to 100, random or block copolymers comprising oxyethylenated chains of formula $(C_2H_4O)_n$ and oxypropylenated chains of formula $(C_3H_6O)_{n'}$, such that the sum of n and n' ranges from 2 to 100, oxyethylenated and/or oxypropylenated glucose groups comprising on average from 4 to 100 oxyethylenated and/or oxypropylenated units distributed over all the hydroxyl functions, oxyethylenated and/or oxypropylenated methylglucose groups comprising on average from 4 to 100 oxyethylenated and/or oxypropylenated units distributed over all the hydroxyl functions.

7. The nanoemulsion of claim 1, wherein the surfactant is selected from the group consisting of hexadecenyl succinate 18 EO, hexadecenyl succinate 45 EO, dihexadecenyl succinate 18 EO, dihexadecenyl succinate of glucose 10 EO, dihexadecenyl succinate of glucose 20 EO, dioctadecenyl succinate of methylglucose 20 EO, and mixtures thereof.

8. The nanoemulsion of claim 1, wherein the oily phase comprises at least 40% by weight of oil(s) having a molecular weight of greater than 400 with respect to the total weight of the oily phase.

9. The nanoemulsion of claim 1, wherein the amount of oily phase comprises 2 to 40% by weight with respect to the total weight of the nanoemulsion.

10. The nanoemulsion of claim 1, further comprising at least one ionic amphiphilic lipid selected from the group consisting of anionic amphiphilic lipids and alkylsulfonic derivatives.

11. The nanoemulsion of claim 10, wherein the ionic amphiphilic lipids are selected from the group consisting of the alkaline salts of dicetyl and dimyristyl phosphate, the alkaline salts of cholesterol sulfate,
the alkaline salts of cholesterol phosphate,
the salts of lipoamino acids,
the sodium salts of phosphatidic acid,
phospholipids,
alkylsulfonic derivatives of formula (V):

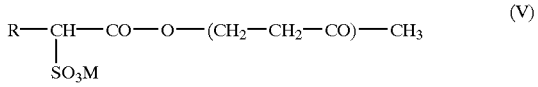

in which R represents $C_6$–$C_{22}$ alkyl radicals, taken as a mixture or separately, and M is an alkali metal, and mixtures thereof.

12. A The nanoemulsion of claim 10, wherein the amount of ionic amphiphilic lipid(s) comprises 0.01 to 5% by weight with respect to the total weight of the nanoemulsion.

13. The nanoemulsion of claim 1, further comprising an additive which improves the transparency selected from the group consisting of lower alcohols, glycols, sugars, and mixtures thereof.

14. The nanoemulsion of claim 13, comprising 0.5 to 20% by weight of the additive with respect to the total weight of the nanoemulsion.

15. The nanoemulsion of claim 1, which comprises a cosmetic, dermatological or ophthalmological active agent.

16. A composition suitable for topical application comprising the nanoemulsion of claim 1.

17. An ophthalmic vehicle, comprising the nanoemulsion of claim 1.

18. A pharmaceutical composition, comprising the nanoemulsion of claim 1.

19. A method of treating dry skin, comprising applying the nanoemulsion of claim 1 to the dry skin.

20. A method of preparing the nanoemulsion of claim 1, comprising:
   mixing the aqueous phase and the oily phase with vigorous stirring at an ambient temperature ranging from 10 to 80° C., and then
   homogenizing the mixture at a pressure ranging from $6 \times 10^7$ Pa to $18 \times 10^7$ Pa.

21. The method of claim 20, wherein the homogenizing of the mixture provides a shearing of from $2 \times 10^6$ $s^{-1}$ to $5 \times 10^8$ $s^{-1}$.

22. A method of caring for, treating or making up skin, face or scalp or a combination thereof, comprising applying the nanoemulsion of claim 1, to the skin, face or scalp or a combination thereof.

23. A method of caring for or treating hair or a combination thereof, comprising applying the nanoemulsion of claim 1, to the hair.

24. A method of caring for or moisturizing skin, mucous membranes or scalp or a combination thereof, comprising applying the nanoemulsion of claim 1, to the skin, mucous membranes or scalp or a combination thereof.

25. The nanoemulsion of claim 5, wherein the oil globules have an average size of 40 to 60 nm.

26. The nanoemulsion of claim 6, wherein n has a value of from 5 to 60.

27. The nanoemulsion of claim 1, wherein n has a value of from 10 to 30.

28. The nanoemulsion of claim 1, wherein the oil with a molecular weight of greater than 400 comprises isocetyl palmitate, isocetyl stearate, avocado oil or jojoba oil.

29. The nanoemulsion of claim 1, wherein the least one oil having a molecular weight of less than 400 comprises isododecane, isohexadecane, isopropyl myristate, silicone oils, isopropyl palmitate or $C_{11}$–$C_{13}$-isoparaffin.

30. The nanoemulsion of claim 1, having a globule size of 55 nm, and a turbidity of 211 NTU.

31. The nanoemulsion of claim 1, which is a gelled, transparent nanoemulsion, having a globule size of 54 nm, and a turbidity of 130 NTU.

* * * * *

UNITED STATES PATENT AND TRADEMARK OFFICE
CERTIFICATE OF CORRECTION

PATENT NO.      : 6,461,625 B1
DATED           : October 8, 2002
INVENTOR(S)     : Jean-Thierry Simonnet et al.

It is certified that error appears in the above-identified patent and that said Letters Patent is hereby corrected as shown below:

<u>Column 9,</u>
Line 13, "$C_6$" should read -- $C_{16}$ --.
Line 16, "A The" should read -- The --.

<u>Column 10,</u>
Line 28, "wherein the least" should read -- wherein at least --.

Signed and Sealed this

Eleventh Day of February, 2003

JAMES E. ROGAN
*Director of the United States Patent and Trademark Office*